(12) United States Patent
Tyler et al.

(10) Patent No.: US 6,733,780 B1
(45) Date of Patent: May 11, 2004

(54) DIRECT COMPRESSION POLYMER TABLET CORE

(75) Inventors: Joseph Tyler, Somerville, MA (US); John S. Petersen, Acton, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/691,429

(22) Filed: Oct. 18, 2000

Related U.S. Application Data

(60) Provisional application No. 60/160,258, filed on Oct. 19, 1999, and provisional application No. 60/174,227, filed on Jan. 3, 2000.

(51) Int. Cl.$^7$ ............................................. A61K 9/20
(52) U.S. Cl. ...................... 424/464; 424/78.08; 424/474
(58) Field of Search ........................... 424/78.11, 78.16, 424/78.08, 78.12, 426, 468

(56) References Cited

U.S. PATENT DOCUMENTS

| | | | |
|---|---|---|---|
| 3,383,236 A | 5/1968 | Brindamour | 117/100 |
| 3,431,138 A | 3/1969 | Zingerman et al. | 117/100 |
| 3,539,380 A | 11/1970 | Johnson et al. | 117/100 |
| 4,115,537 A | 9/1978 | Driscoll et al. | 424/1 |
| 4,211,763 A | 7/1980 | Marshall et al. | 424/1 |
| 4,302,440 A * | 11/1981 | John et al. | 424/480 |
| 4,341,563 A | 7/1982 | Kurihara et al. | 106/171 |
| 4,543,370 A | 9/1985 | Porter et al. | 523/100 |
| 4,631,305 A | 12/1986 | Guyer et al. | 523/400 |
| 4,849,227 A | 7/1989 | Cho | 424/498 |
| 4,956,182 A | 9/1990 | Bequette et al. | 424/476 |
| 4,983,398 A | 1/1991 | Gaylord et al. | 424/465 |
| 4,983,399 A | 1/1991 | Maish | 424/465 |
| 5,073,380 A | 12/1991 | Babu et al. | 424/472 |
| 5,194,464 A | 3/1993 | Itoh et al. | 524/42 |
| 5,262,167 A | 11/1993 | Vegesna et al. | 424/439 |
| 5,401,515 A | 3/1995 | Woodard et al. | 424/475 |
| 5,447,726 A | 9/1995 | Nomura | 424/464 |
| 5,455,047 A | 10/1995 | Bequette et al. | 424/476 |
| 5,487,888 A | 1/1996 | Mandeville et al. | 424/78.1 |
| 5,496,545 A * | 3/1996 | Holmes-Farley et al. | 424/78.11 |
| 5,520,932 A | 5/1996 | McCurdy et al. | 424/501 |
| 5,607,669 A | 3/1997 | Mandeville et al. | 424/78.12 |
| 5,618,530 A | 4/1997 | Mandeville et al. | 424/78.12 |
| 5,624,963 A | 4/1997 | Mandeville et al. | 514/789 |
| 5,654,003 A | 8/1997 | Fuisz et al. | 424/469 |
| 5,667,775 A | 9/1997 | Holmes-Farley et al. | 424/78.11 |
| 5,679,717 A | 10/1997 | Mandeville et al. | 514/742 |
| 5,686,106 A | 11/1997 | Kelm et al. | 424/463 |
| 5,693,675 A | 12/1997 | Mandeville et al. | 514/742 |
| 5,702,696 A | 12/1997 | Mandeville et al. | 424/78.12 |
| 5,703,188 A | 12/1997 | Mandeville et al. | 526/290 |
| 5,709,880 A | 1/1998 | Del Corral et al. | 424/464 |
| 5,718,920 A | 2/1998 | Notenbomber | 424/489 |
| 5,747,067 A | 5/1998 | Auguello et al. | 424/464 |
| 5,750,148 A | 5/1998 | Maruyama et al. | 424/494 |
| 5,807,582 A | 9/1998 | Cha | 424/489 |
| 5,814,336 A | 9/1998 | Kelm et al. | 424/463 |
| 5,840,339 A | 11/1998 | Kunin | 424/489 |
| 5,840,766 A | 11/1998 | Mandeville et al. | 514/742 |
| 5,985,938 A | 11/1999 | Holmes-Farley et al. | 514/789 |
| 6,034,129 A | 3/2000 | Mandeville et al. | 514/549 |
| 6,083,495 A | 7/2000 | Holmes-Farley et al. | 424/78.11 |
| 6,264,937 B1 * | 7/2001 | Mandeville et al. | 424/78.35 |

FOREIGN PATENT DOCUMENTS

| | | |
|---|---|---|
| EP | 0 997 148 A1 | 5/2000 |
| WO | WO 93/00915 | 1/1993 |
| WO | WO98/29107 | 7/1998 |
| WO | WO 98/44933 | 10/1998 |
| WO | WO99/22721 | 5/1999 |
| WO | WO 00/22008 | 4/2000 |

OTHER PUBLICATIONS

Physicians Desk Reference "Renagel".*
U.S. Ser. No.: 09/359,226, filed Jul. 22, 1999.
U.S. Ser. No.: 09/668,874, filed Sep. 25, 2000.
U.S. Ser. No.: 09/542,329, filed Apr. 04, 2000.
U.S. Ser. No.: 08/956,572, filed Oct. 23, 1997.
U.S. Ser. No.: 09/406,311, filed Sep. 27, 1999.
U.S. Ser. No.: 09/655,998, filed Sep. 6, 2000.
U.S. Ser. No.: 08/979,096, filed Nov. 26, 1997.
U.S. Ser. No.: 09/359,226, filed Jul. 22, 1999.
U.S. Ser. No.: 08/777,408, filed Dec. 30, 1996.
U.S. Ser. No.: 08/964,498, filed Nov. 5, 1997.

* cited by examiner

Primary Examiner—Thurman K. Page
Assistant Examiner—Konata M. George
(74) Attorney, Agent, or Firm—Hamilton, Brook, Smith & Reynolds, P.C.

(57) ABSTRACT

The present invention provides a tablet core which comprises at least about 95% by weight of an aliphatic amine polymer. The invention also provides a method of producing a tablet core comprising at least about 95% by weight of an aliphatic amine polymer resin. The method comprises the step of compressing the aliphatic amine polymer to form the tablet core. The tablet core can further include one or more excipients. In this embodiment the method of producing the tablet core comprises the steps of: (1) hydrating the aliphatic amine polymer to the desired moisture level; (2) blending the aliphatic amine polymer with the excipients in amounts such that the polymer comprises at least about 95% by weight of the resulting blend; and (3) compressing the blend to form the tablet core. The present invention further relates to a coated tablet comprising an aliphatic amine polymer core wherein the coating is a water based coating.

19 Claims, 1 Drawing Sheet

The Figure

| Run No. | Actual Moisture Content (%LOD) | Stearic Acid (%) | Aerosil (%) | Lubricant Blend Time (min.) | Compression Force (kg) | Hardness (N) | Friability (%) | Disintegral Time (min) | Flow rate (g/sec.) | Thickness (inch x 1000) |
|---|---|---|---|---|---|---|---|---|---|---|
| 5 | 8.11 | 0.5 | 0.25 | 2 | 2000 | 228 | 0.25 | 6.58 | 0.619 | 306 |
| 7 | 8.139 | 0.25 | 0.5 | 2 | 2000 | 321 | 0.25 | 5.6 | 0.511 | 303 |
| 11 | 8.21 | 0.25 | 0.25 | 7 | 2000 | 248 | 0.12 | 5.24 | 0.619 | 305 |
| 17 | 7.998 | 0.5 | 0.5 | 7 | 2000 | 156 | 0.25 | 3.84 | 0.549 | 308 |
| 19 | 7.94 | 0.375 | 0.375 | 4.5 | 1750 | 181 | 0.25 | 2.31 | 0.582 | 309 |
| 3 | 8.328 | 0.25 | 0.25 | 2 | 1500 | 184 | 0 | 5.88 | 0.61 | 312 |
| 9 | 7.963 | 0.5 | 0.5 | 2 | 1500 | 149 | 0.25 | 5.12 | 0.495 | 312 |
| 13 | 8.098 | 0.5 | 0.25 | 7 | 1500 | 146 | 0.16 | 4.54 | 0.669 | 313 |
| 15 | 8.247 | 0.25 | 0.5 | 7 | 1500 | 149 | 0.31 | 5.17 | 0.543 | 316 |
| 27 | 6.576 | 0.375 | 0.375 | 4.5 | 2000 | 152 | 0.5 | 3.27 | 0.47 | 309 |
| 20 | 6.584 | 0.25 | 0.375 | 4.5 | 1750 | 170 | 0.38 | 3.12 | 0.503 | 313 |
| 22 | 6.509 | 0.375 | 0.25 | 4.5 | 1750 | 134 | 0.5 | 3.6 | 0.557 | 314 |
| 24 | 6.674 | 0.375 | 0.375 | 2 | 1750 | 167 | 1.25 | 3.24 | 0.525 | 313 |
| 1 | 6.716 | 0.375 | 0.375 | 4.5 | 1750 | 116 | 1.27 | 3.66 | 0.509 | 313 |
| 28 | 6.615 | 0.375 | 0.375 | 4.5 | 1750 | 129 | 0.88 | 2.6 | 0.514 | 315 |
| 29 | 6.555 | 0.375 | 0.375 | 4.5 | 1750 | 120 | 1.27 | 2.77 | 0.526 | 317 |
| 25 | 6.682 | 0.375 | 0.375 | 7 | 1750 | 106 | 1.76 | 6.39 | 0.519 | 315 |
| 23 | 6.509 | 0.5 | 0.375 | 4.5 | 1750 | 130 | 1.25 | 3.91 | 0.492 | 315 |
| 21 | 6.636 | 0.375 | 0.5 | 4.5 | 1750 | 111 | 1.87 | 3.37 | 0.513 | 317 |
| 26 | 6.54 | 0.375 | 0.375 | 4.5 | 1500 | 96 | 2.02 | 3.12 | 0.531 | 322 |
| 2 | 5.57 | 0.25 | 0.25 | 2 | 2000 | 181 | 0.25 | 4.22 | 0.478 | 311 |
| 8 | 5.079 | 0.5 | 0.5 | 2 | 2000 | 134 | 0.87 | 3.1 | 0.319 | 316 |
| 12 | 5.068 | 0.25 | 0.5 | 7 | 2000 | 85 | 3.25 | 2.25 | 0.474 | 319 |
| 14 | 4.914 | 0.5 | 0.25 | 7 | 2000 | 129 | 1.02 | 3.78 | 0.439 | 318 |
| 18 | 4.932 | 0.375 | 0.375 | 4.5 | 1750 | 104 | 2.01 | 2.85 | 0.406 | 322 |
| 4 | 5.034 | 0.5 | 0.5 | 2 | 1500 | 74 | 3.78 | 3.02 | 0.451 | 329 |
| 6 | 4.892 | 0.25 | 0.25 | 2 | 1500 | 128 | 1 | 3.67 | 0.366 | 328 |
| 10 | 5.211 | 0.5 | 0.25 | 7 | 1500 | 80 | 3.06 | 1.21 | 0.461 | 327 |
| 16 | 5.32 | 0.25 | 0.5 | 7 | 1500 | 45 | 5.99 | 1.03 | 0.384 | 331 |

DIRECT COMPRESSION POLYMER TABLET CORE

RELATED APPLICATION

This application claims the benefit of U.S. Provisional Application No. 60/160,258, filed Oct. 19, 1999, and U.S. Provisional Application No. 60/174,227, filed Jan. 3, 2000. The entire teachings of which are incorporated herein by reference.

BACKGROUND OF THE INVENTION

A number of polymeric materials having useful therapeutic activity have been described for treatment of various conditions such as hyperlipidemia and hyperphosphatemia. Many of these polymeric materials function as non-absorbed ion exchange resins in the digestive tract. Such non-absorbed polymeric materials bind or otherwise sequester a target molecule and facilitate its removal from the body via the gastrointestinal tract. Examples of such resins include: Colestipol and Cholestyramine useful as orally administered cholesterol lowering agents; a variety of aliphatic amine polymers disclosed U.S. Pat. Nos. 5,496,545 and 5,667,775 useful as phosphate binders particularly for removing phosphate from patients suffering from renal failure; and other aliphatic amine polymers disclosed in U.S. Pat. No. 5,624,963, U.S. Pat. No. 5,679,717, WO98/29107 and WO99/22721 useful as cholesterol lowering agents.

Non-absorbed polymer therapeutics have traditionally presented a number of formulation challenges as the dosages are generally very large (gram quantities), and the resins tend to be extremely hydrophilic. The most desirable formulation for oral delivery of a therapeutic is a direct compression tablet formulation. However, not all therapeutics, particularly given the high dose requirements of polymeric ion exchange therapeutics, lend themselves to a tablet formulation. Even if such materials could be rendered into a tablet, it is generally not possible without the significant addition of other materials which assist in the tableting process. Ultimately the addition of any materials other than the active ingredient is undesirable given the dose requirement of the active ingredient. Ideally the tablet should contain as much active ingredient as possible with little else in the way of additional materials such that the tablet is as small as possible and easy to administer to the patient.

In addition, once the polymeric materials are compressed into a tablet, the tablet requires a coating for ease of administration to the patient. It has been discovered that the core polymeric material tends to be very hygroscopic, and thus will swell immediately upon contact with the inside of the mouth. Most coatings contain water, and thus it was believed that coating such tablets with a water-based coating would be impossible because the hygroscopic tablets would swell during the coating process. Thus providing a tablet core comprising a hygroscopic material such that a suitable coating may be used in conjunction with that core, is another significant challenge to providing the polymeric active ingredient in tablet form.

There is a need to provide suitable dosage forms for polymeric ion exchange materials, particularly for hydrophilic aliphatic amine polymers useful as therapeutic agents, which minimize the overall amount of material administered to the patient, which are easy to administer orally, and which are stable upon production and storage.

SUMMARY OF THE INVENTION

The present invention provides a tablet core which comprises at least about 95% by weight of an aliphatic amine polymer. In a preferred embodiment, the aliphatic amine polymer resin is a cross-linked polyallylamine resin. The aliphatic amine polymer is preferably hydrated. The hydrated polymer can, for example, comprise from about 5% water by weight or greater.

The invention also provides a method of producing a tablet core comprising at least about 95% by weight of an aliphatic amine polymer resin. The method comprises the step of compressing the aliphatic amine polymer to form the tablet core. The tablet core can further include one or more excipients. In this embodiment, the method of producing the tablet core comprises the steps of: (1) hydrating or drying the aliphatic amine polymer to the desired moisture level; (2) blending the aliphatic amine polymer with the excipients in amounts such that the polymer comprises at least about 95% by weight of the resulting blend; and (3) compressing the blend to form the tablet core. The present invention further relates to a coated tablet wherein the coating comprises a water based coating.

BRIEF DESCRIPTION OF THE DRAWINGS

The FIGURE is a table comprising data showing formulations and responses for sevelamer hydrochloride compressed tablet cores.

DETAILED DESCRIPTION OF THE INVENTION

A number of polymeric materials having useful therapeutic activity have been discussed above. In particular, aliphatic amine polymers have been disclosed which are useful in methods of lowering the serum phosphate level of a patient and lowering the serum cholesterol level of a patient. For example an epichorohydrin-cross-linked poly (allylamine hydrochloride) resin (U.S. Pat. Nos. 5,496,545 and 5,667,775), also referred to as sevelamer hydrochloride or sevelamer and marketed as RENAGEL®, has been shown to be effective at removing phosphate from human patients suffering from renal failure. Therapeutically effective dosages of sevelamer hydrochloride are large, typically on the order of 4 to 6 grams per day. Consequently, development of a dosage form of this and similar resins which minimizes the amount of excipient material is desirable.

The present invention provides a tablet core comprising at least about 95% by weight of an aliphatic amine polymer. The aliphatic amine polymer resin can be any of the aliphatic amine resins described in U.S. Pat. Nos. 5,496,545; 5,667,775; 5,624,963; 5,703,188; 5,679,717; 5,693,675, 5,607,669; 5,618,530; 5,487,888; and 5,702,696, each of which is hereby incorporated herein by reference in its entirety. Other suitable aliphatic amine polymers are disclosed in U.S. Ser. Nos. 08/670,764; 08/959,471, and 08/979,096, each of which is hereby incorporated by reference herein in its entirety. In a particularly preferred embodiment, the aliphatic amine polymer is polyallylamine, polyvinylamine, poly(diallylamine) or poly(ethyleneimine) or a salt thereof with a pharmaceutically acceptable acid. The aliphatic amine polymer is optionally substituted at one or more nitrogen atoms with an alkyl group or a substituted alkyl group such as a trialkylammonioalkyl group. The aliphatic amine polymer can optionally be cross-linked, for example via a multifunctional monomer or a bridging group which connects two amino nitrogen atoms from two different polymer strands. In a preferred embodiment, the aliphatic amine polymer resin is hydrated. For sevelamer hydrochloride, in particular, the compressibility is strongly dependent upon the degree of hydration (moisture content)

of the resin. Preferably, the resin has a moisture content of about 5% by weight or greater, more preferably, the moisture content is from about 5% to about 9% by weight, and most preferably about 7% by weight. It is to be understood that in embodiments in which the polymer resin is hydrated, the water of hydration is considered to be a component of the resin. Thus, in this embodiment, the tablet core comprises at least about 95%, preferably at least about 96%, and more preferably at least about 98% by weight of the hydrated polymer, including the water of hydration.

The tablet can further comprise one or more excipients, such as hardeners, glidants and lubricants, which are well known in the art. Suitable excipients include colloidal silicon dioxide, stearic acid, magnesium silicate, calcium silicate, sucrose, calcium stearate, glyceryl behenate, magnesium stearate, talc, zinc stearate and sodium stearylfumarate. The excipients can represent from 0 to about 5% of the tablet core by weight.

The tablet core of the invention is prepared by a method comprising the steps of: (1) hydrating or drying the aliphatic amine polymer to the desired moisture level; (2) blending the aliphatic amine polymer with any excipients to be included in amounts such that the polymer comprises at least about 95% by weight of the resulting blend; and (3) compressing the blend using conventional tableting technology.

The invention also relates to a stable, swallowable coated tablet, particularly a tablet comprising a hydrophilic core, such as a tablet comprising an aliphatic amine polymer, as described above. In one embodiment, the coating composition comprises a cellulose derivative and a plasticizing agent. The cellulose derivative is, preferably, hydroxypropylmethylcellulose (HPMC). The cellulose derivative can be present as an aqueous solution. Suitable hydroxypropylmethylcellulose solutions include those containing HPMC low viscosity and/or HPMC high viscosity. Additional suitable cellulose derivatives include cellulose ethers useful in film coating formulations. The plasticizing agent can be, for example, an acetylated monoglyceride such as diacetylated monoglyceride, The coating composition can further include a pigment selected to provide a tablet coating of the desired color. For example, to produce a white coating, a white pigment can be selected, such as titanium dioxide.

In one embodiment, the coated tablet of the invention can be prepared by a method comprising the step of contacting a tablet core of the invention, as described above, with a coating solution comprising a solvent, at least one coating agent dissolved or suspended in the solvent and, optionally, one or more plasticizing agents. Preferably, the solvent is an aqueous solvent, such as water or an aqueous buffer, or a mixed aqueous/organic solvent. Preferred coating agents include cellulose derivatives, such as hydroxypropylmethylcellulose. Typically, the tablet core is contacted with the coating solution until the weight of the tablet core has increased by an amount ranging from about 4% to about 6%, indicating the deposition of a suitable coating on the tablet core to form a coated tablet.

In one preferred embodiment, the solids composition of the coating solution is:

| Material | % W/W |
|---|---|
| HPMC low viscosity Type 2910, cUSP | 38.5% |
| HPMCE high viscosity Type 2910, cUSP | 38.5% |
| diacetylated monoglyceride | 23.0% |

Tablets may be coated in a rotary pan coater as is known in the art or any other conventional coating apparatus such as a column coater or a continuous coater.

Astonishingly, it has been found that an aqueous coating dispersion is suitable as a coating solution for tablets comprising a hygroscopic, or water-swellable substance, such as an aliphatic amine polymer tablet. For example, the coating composition provides a strong, elastic and moisture-permeable coating without causing significant concomitant swelling of the tablet core during the coating process. In a preferred embodiment, the coating composition provides a tablet coating which withstands the swelling and contraction of sevelamer hydrochloride tablets during exposure to varying humidity levels and other known stability tests. Further, the coating composition can be used to coat other aliphatic amine polymer tablets without excessive uptake by the tablet core of water from the coating solution during the coating process.

The present invention also relates to the use of an aliphatic amine polymer as a disintegrant in a tablet. In general, in this embodiment the aliphatic amine polymer is not the active ingredient in the tablet, but is added to the tablet to enhance the rate of disintegration of the tablet following administration. This allows a more rapid release of the active agent or agents. The tablet will generally include the aliphatic amine polymer, one or more active ingredients, such as therapeutic agents (medicaments), and, optionally, one or more additional excipients.

The aliphatic amine polymer can be one of the aliphatic amine polymers disclosed above, such as polyethyleneimine, polyvinylamine, polyallylamine, polydiallylamine or any of the aliphatic amine polymers disclosed in U.S. Pat. Nos. 5,496,545 and 5,667,775 and U.S. Ser. Nos. 08/777,408 and 08/964,498, the teachings of each of which are incorporated herein by reference. In one embodiment, the aliphatic amine polymer is a cross-linked polyallylamine or a salt thereof with a pharmaceutically acceptable acid. Preferably, the aliphatic amine polymer is an epichlorohydrin-cross-linked polyallylamine or salt thereof with a pharmaceutically acceptable acid, such as sevelamer or sevelamer hydrochloride.

The tablet which includes an aliphatic amine as a disintegrant will, generally, include a sufficient amount of the aliphatic amine polymer to effectively enhance the rate of tablet disintegration under conditions of use. For example, if the tablet is an oral doseage form and it is desired that the tablet disintegrate in the stomach of the patient, the tablet should include a sufficient amount of the polymer to enhance the disintegration rate of the tablet under the conditions encountered in the stomach. The appropriate amount of the polymer to be included in the tablet can be determined by one skilled in the art using known methods. Typically, the polymer, the active ingredient or ingredients and any additional fillers or excipients are combined by mixing, and the resulting mixture is compressed to form a tablet using conventional methods. The tablet core formed in this way can then be coated, for example, as described above, or by other methods and other coating compositions which are known in the art and suitable for the intended use of the tablet.

In one embodiment, the tablet which includes an aliphatic amine polymer as a disintegrant is intended for administration in vivo, for example, to a patient, such as a human. Preferably, the tablet is intended to be administered orally. In this embodiment, the active ingredient or ingredients will be a therapeutic or diagnostic agent. The tablet can also be intended for use in vitro, for example, to deliver an active ingredient to an aqueous environment, such as a swimming pool.

The invention will now be described in detail by reference to the following examples.

EXAMPLES

Example 1

Preparation and Characterization of 400 mg and 800 mg Sevelamer Hydrochloride Direct Compression Tablet Cores

Preparation of Tablet Cores 400 mg sevelamer hydrochloride tablet cores were prepared from a blend consisting of 5000.0 g sevelamer hydrochloride, 50.0 g colloidal silicon dioxide, NF (Aerosil 200) and 50.0 g stearic acid. The sevelamer hydrochloride was hydrated to moisture content of 6% by weight. The blend was prepared by passing the sevelamer hydrochloride and colloidal silicon dioxide through a #20 mesh screen, transferring the mixture to a 16 quart PK blender and blending for five minutes. The stearic acid was then passed through an oscillator equipped with a #30 mesh screen, transferred into the 16 quart PK blender and blended for five minutes with the sevelamer hydrochloride/colloidal silicon dioxide mixture. The resulting blend was discharged into a drum and weighed. The final blend was then compressed on a 16 station Manesty B3B at 4 tons pressure using 0.280"×0.620" punches to give tablet cores with an average weight of 434 mg. The resulting tablets consisted of 425 mg 6% hydrated sevelamer hydrochloride (equivalent to 400 mg anhydrous sevelamer hydrochloride), 4.25 mg colloidal silicon dioxide and 4.25 mg stearic acid.

800 mg sevelamer hydrochloride tablet cores were prepared from 19.0 kg sevelamer hydrochloride, 0.19 kg colloidal silicon dioxide, and 0.19 kg stearic acid,. The sevelamer hydrochloride had a moisture content of 6% by weight. The blend was prepared by passing the sevelamer hydrochloride and colloidal silicon dioxide through a #20 mesh screen, transferring the mixture to a PK blender and blending for five minutes. The stearic acid was then passed through an oscillator equipped with a #30 mesh screen, transferred into the PK blender and blended for five minutes with the sevelamer hydrochloride/colloidal silicon dioxide mixture. The resulting blend was then discharged into a drum and weighed. The final blend was then compressed in on a 16 station Manesty B3B at 4 tons pressure using 0.3125"×0.750" punches to give tablets with an average weight of 866 mg. The resulting tablets consisted of 850 mg 6% hydrated sevelamer hydrochloride (equivalent to 800 mg anhydrous sevelamer hydrochloride), 8.0 mg colloidal silicon dioxide and 8.0 mg stearic acid.

Characterization of Tablet Cores

The tablets prepared as described above were white to off-white, oval shaped, compressed tablets. The variation of the tablets prepared from each blend with respect to weight, thickness, friability, hardness, disintegration time and density was assessed. Standard methods in the art were employed for each of the measurements. The results, (not shown), indicate that the hardness, friability, thickness, and disintegration behavior of the sevelamer hydrochloride tablets all met industry-standard criteria.

Example 2

Coating of Sevelamer Hydrochloride Tablet Cores

Compressed core tablets prepared as described in Example 1 were coated in a coating pan with an aqueous coating solution having a solids composition comprising:

| Material | % W/W |
|---|---|
| HPMC low viscosity Type 2910, cUSP | 38.5% |
| HPMCE high viscosity Type 2910, cUSP | 38.5% |
| diacetylated monoglyceride | 23.0% |

The coating solution was applied to the compressed cores until a weight gain of approximately 4 to 6% was achieved. Stability studies—controlled room temperature, accelerated conditions, freeze/thaw and photosensitivity—for the coated sevelamer hydrochloride tablets were conducted in accordance with those procedures known in the art and described in the following references: International Committee on Harmonization (ICH) guidance "Q1A—Stability Testing of New Drug Substances and Products" (June 1997); ICH "Q1B—Guidelines for the Photostability Testing of New Drug Substances and Products" (November 1996); and ICH guidance "Q1C—Stability Testing for New Dosage Forms" (November 1996. The results (not shown) indicate that the coated tablets all met industry standard criteria.

Example 3

Factors Affecting the Processing and Performance Characteristics of Compressed Tablets (Prior to Coating)

In order to maintain consistently acceptable compressed tablet on a per batch basis, a number of correlative tests were performed in order to determine which factors most strongly impact the quality and integrity of the tablets. Studies such as weight variation, tablet hardness, friability, thickness, disintegration time, among others are known to those skilled in the art and are described in the United States Pharmacopeia. (U.S.P.). "Hardness" means the measure of the force (measured herein in Newtons) needed to fracture a tablet when such tablet is placed lengthwise on a Hardness Tester. "Friability" is the measure of the mechanical strength of the tablet needed to withstand the rolling action of a coating pan and packaging. It is measured using a friabiliator. "Thickness" is the measure of the height of the tablet using a micrometer. "Disintegration Time" is the time necessary for the tablet to break apart in an appropriate solution at 37° C. and is measured in minutes.

Attainment of appropriate hardness (150–170 N hardness range) and friability (no more than 0.8%) is important to the success of the formulation. Having tablets with high hardness and low friability is particularly important when the tablets are to be coated as is the case with sevelamer hydrochloride tablets.

The FIGURE provides a table listing several different sevelamer hydrochloride tablet core formulations that vary by a number of factors including (actual) moisture content, and compression force used, excipient content among other variations. The data in The FIGURE indicates that the most important factor affecting the processing and performance characteristics of compressed tablets is the moisture content. All formulations provided good flow with little weight variation throughout the entire range of compositions. In addition, disintegration times were less than 5 minutes across the range of compositions. Thus, it appears that moisture content and compression force provide the most appropriate factors on which to establish operating ranges for hardness and friability.

Equivalents

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A tablet comprising a core and a coating thereof, wherein at least about 95% by weight of the core is an aliphatic amine polymer selected from the group consisting of unsubstituted and N-substituted poly(allylamine), poly(diallylamine), and poly(vinylamine).

2. The tablet of claim 1 wherein the N-substituents are selected from the group consisting of substituted and unsubstituted $C_1$–$C_{24}$-alkyl groups.

3. The tablet of claim 2 wherein the alkyl substituents are trialkylammonioalkyl groups.

4. The tablet of claim 1 wherein the aliphatic a polymer is cross-linked.

5. The tablet of claim 1 comprising one or more excipients.

6. A tablet comprising a core and a coating therefor, wherein at least about 95% by weight of the core is a linear or cross-linked poly(allylamine) or a pharmaceutically acceptable salt thereof.

7. The tablet of claim 6 wherein the poly(allylamine) is hydrated.

8. The tablet of claim 7 wherein the poly(allylamine) comprises from about 3% to about 10% water.

9. The tablet of claim 8 wherein thee poly(allylamine) comprises from about 5% to about 8% water.

10. The tablet of claim 9 wherein the polyallylamine is from about 1% to about 10% cross-linked.

11. A tablet comprising a core and a coating therefor, wherein at least about 95% by weight of the core is a hydrated cross-linked poly(allylamine hydrochloride).

12. The tablet of claim 1 wherein the coating is a water-based coating.

13. The tablet of claim 6 wherein the coating is a water-based coating.

14. The tablet of claim 13 wherein said water-based coating comprises hydroxypropylmethylcellulose and a plasticizer.

15. The tablet of claim 14 wherein said water-based coating comprises hydroxypropylmethylcellulose low viscosity, hydroxypropylmethylcellulose high viscosity, and diacetylated monoglyceride.

16. The tablet of claim 1 wherein said polymer is polydiallylamine.

17. The tablet of claim 16 wherein said tablet further comprises a water-based coating.

18. A tablet comprising a core and a coating therefor, wherein at least about 95% by weight of the core is a linear or cross-linked poly(allylamine) or a pharmaceutically acceptable salt thereof, wherein the moisture content of the poly(allylamine) is from about 5% to about 9% by weight, wherein the hardness of the tablet is at least about 150 N and wherein the friability of the tablet is no more than 0.8%.

19. A tablet comprising a core and a coating therefor, wherein the core comprises 98% by weight sevelamer hydrochloride with a moisture content of 6% by weight, 1% by weight colloidal silicon dioxide and 1% by weight stearic acid, and wherein the coating is a mixture comprising 38.5% w/w low viscosity hydroxypropylmethylcellulose, 38.5% high viscosity hydroxypropylmethylcellulose and 23% w/w diacetylated monoglyceride.

* * * * *